US005300529A

United States Patent [19]

Narayanan

[11] Patent Number: 5,300,529
[45] Date of Patent: Apr. 5, 1994

[54] STABLE, CLEAR, EFFICACIOUS AQUEOUS MICROEMULSION COMPOSITIONS CONTAINING A HIGH LOADING OF A WATER-INSOLUBLE, AGRICULTURALLY ACTIVE CHEMICAL

[75] Inventor: Kolazi S. Narayanan, Palisades Park, N.J.

[73] Assignee: ISP Investments Inc., Wilmington, Del.

[21] Appl. No.: 8,946

[22] Filed: Jan. 26, 1993

Related U.S. Application Data

[63] Continuation-in-part of Ser. No. 978,860, Nov. 19, 1992, which is a continuation-in-part of Ser. No. 964,245, Oct. 21, 1992, abandoned, which is a continuation-in-part of Ser. No. 654,250, Feb. 12, 1991, abandoned.

[51] Int. Cl.$^5$ ............................................. A01N 25/00
[52] U.S. Cl. ................................................ 514/788
[58] Field of Search ........................ 504/116; 514/788

[56] References Cited

FOREIGN PATENT DOCUMENTS 0695393 8/1968 South Africa .
8800184 1/1988 World Int. Prop. O. .

OTHER PUBLICATIONS

Chemical Abstracts (109:131269m) 1988.

*Primary Examiner*—Frederick E. Waddell
*Assistant Examiner*—Kevin E. Weddington
*Attorney, Agent, or Firm*—Walter Katz; Marilyn J. Maue; Joshua J. Ward

[57] ABSTRACT

An Inert Matrix Composition (IMC) is provided for forming a stable, clear, efficacious Microemulsion Concentrate (MEC) including about 2–30%, preferably 5–25%, by weight of the composition, of a water-insoluble Agriculturally Active Chemical (AAC). Upon dilution of the concentrate with water, an Aqueous Microemulsion (AME) is provided. The IMC consists essentially of:

(a) a $C_6$–$C_{18}$ alkyl pyrrolidone in an amount sufficient to form micelles of the AAC solvated in water;

(b) a $C_1$–$C_4$ alkyl pyrrolidone in an amount sufficient to complex with said $C_6$–$C_{18}$ alkyl pyrrolidone and to solubilize the AAC in the micelles;

(c) a nonionic surfactant having an HLB of $\geq 6$ in an amount sufficient to complex with the $C_6$–$C_{18}$ alkyl pyrrolidone to reduce the micelle size to about 0.005–0.5 microns, preferably 0.01–0.1 microns, thereby precluding disadvantageous leakage of the solvated AAC through the micelles; and (d) optionally, an anionic surfactant to enhance the close packing of the micelles, thereby rendering the compositions more stable as evidenced by the presence of a clear, homogeneous liquid phase.

In the MEC, the weight ratio of AAC to (a)+(c)+(d) is 1:1 to 1:20, preferably 1:3 to 1:10; and AAC to (b) is about 1:0.1 to 1:90, preferably 1:0.5 to 1:5.

10 Claims, No Drawings

STABLE, CLEAR, EFFICACIOUS AQUEOUS MICROEMULSION COMPOSITIONS CONTAINING A HIGH LOADING OF A WATER-INSOLUBLE, AGRICULTURALLY ACTIVE CHEMICAL

CROSS-REFERENCE TO RELATED U.S. PATENT APPLICATIONS

This application is a continuation-in-part of application Ser. No. 978,860, filed Nov. 19, 1992, which is a continuation-in-part of Ser. No. 964,245, filed Oct. 21, 1992, now abandoned which, in turn, is a continuation-in-part of application Ser. No. 654,250, filed Feb. 12, 1991.

BACKGROUND OF THE INVENTION

1. Field of the Invention

The invention relates to a delivery system for water-insoluble, agriculturally active chemicals (AAC), and, more particularly, to an inert matrix composition (IMC) for forming both a microemulsion concentrate (MEC) and an aqueous microemulsion (AME) containing high loadings of such chemicals.

2. Description of the Prior Art

Agriculturally active chemicals are most preferably applied in the form of aqueous emulsions, solutions, or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into a macroemulsion (sometimes referred to herein as an emulsion), it is difficult to maintain the emulsified state. This, in turn, creates problems in maintaining a uniform formulation, particularly, when the formulation is diluted with water for application to the plants.

An attempt to provide concentrates of agriculturally useful chemicals for producing macroemulsions was disclosed in South African Patent Application No. 695,393, filed Jul. 25, 1969. This application was directed to the formulation of a concentrate substantially water-insoluble pesticides for agricultural use. The pesticides, either in oil or solid form, were mixed with pyrrolidones having a hydrogen or a lower alkyl group containing from 1 to 4 carbon atoms attached to the nitrogen atom of the pyrrolidone ring. The application disclosed that concentrated solutions of difficult to dissolve pesticides could be formulated and that such concentrates exhibited good stability. The concentrates utilized were those containing the pesticidal active ingredient, the particular lower alkyl pyrrolidone, a co-solvent which is usually a common organic solvent, such as, an aromatic including xylene, methylated and polyalkylated naphthalenes and aliphatic solvents, and a dispersing or emulsifying agent, such as, a surfactant, including polyoxyethylene alkylphenols, polyoxyethylene fatty esters, polyoxyethylene sorbitan fatty esters which may be blended with oil-soluble sulfonates, calcium and aminosulfonate salts, and the like.

However, this prior art did not offer a solution to the problem arising from the difficulty in maintaining the stability of the emulsion formed after the concentrate was diluted with water. Consequently, unless the diluted form of the concentrate was used immediately after emulsification, it was difficult to provide a stable diluted formulation for application to the plants, soil, pests, and the like.

In addition, for such agricultural uses, it is also desirable to avoid the use of toxic solvents, including those of Lists 1 and 2 of 40 C.F.R. 154.7 dated Apr. 22, 1987, which includes inerts of toxicological concern and solvents having high flash points, as well as to increase the amount of the agriculturally active material in the concentrate. Moreover, many organic solvents which have been used in the past, even those exhibiting relatively low toxicities, are not biodegradable and thus remain as a pollutant.

The Parent Applications referred to hereinabove have provided solutions to the problem of providing stable macroemulsions of insoluble agricultural chemicals in aqueous systems. This was accomplished by the use of long and short chain alkyl lactams for formation of emulsifiable concentrates of agricultural chemicals. See also U.S. Pat. No. 5,093,031, the contents of which are incorporated herein by reference, which disclosed the use of long chain alkyl lactams to prepare emulsifiable concentrates of water-insoluble, agriculturally active ingredients, e.g., herbicides, fungicides, pesticides, and the like, which on dilution with water, formed stable macroemulsions.

More particularly, Narayanan, in U.S. Pat. No. 5,071,463, described an emulsifiable concentrate comprising a macroemulsion of an agriculturally active chemical, N-methyl pyrrolidone, N-octyl pyrrolidone and an anionic surfactant such as Gafac RE-610 (an ethoxylated phosphate ester). Only a small amount of anionic surfactant was required to form a macroemulsion with up to 40% by weight of the active chemical. However, the macroemulsion was cloudy and it was necessary to use the aqueous macroemulsion soon after preparation.

Accordingly, it is an object of this invention to provide an aqueous microemulsion in which relatively high loadings of the water-insoluble, agriculturally active chemical can be accommodated in the micelles of the microemulsion, which are clear, stable and efficacious, and, particularly, in which both the microemulsion concentrate (before dilution with water) and the aqueous microemulsion (after dilution with water) can be stored indefinitely at or below room temperature before use.

Another object herein is to provide an inert matrix composition from which the microemulsion concentrate and the aqueous microemulsion can be prepared conveniently.

A particular object of this invention is to provide an aqueous microemulsion of a water-insoluble, agriculturally active chemical at a high chemical loading which is solvated and stable within a close packed micelle of predetermined dimensions.

SUMMARY OF THE INVENTION

An Inert Matrix Composition (IMC) is provided for forming a stable, clear, efficacious Microemulsion Concentrate (MEC) including about 2–30%, preferably 5–25%, by weight of the composition, of a water-insoluble Agriculturally Active Chemical (AAC). Upon dilution of the concentrate with water, an Aqueous Microemulsion (AME) is provided. The IMC consists essentially of:

(a) a $C_8$–$C_{18}$ alkyl pyrrolidone in an amount sufficient to form micelles of the AAC solvated in water;

(b) a $C_1$–$C_4$ alkyl pyrrolidone in an amount sufficient to complex with said $C_6$–$C_{18}$ alkyl pyrrolidone and to solubilize the AAC in the micelles;

(c) a nonionic surfactant having an HLB of $\geq 6$ in an amount sufficient to complex with the $C_6$–$C_{18}$ alkyl pyrrolidone to reduce the micelle size to about 0.005–0.5 microns, preferably 0.01–0.1 microns, thereby precluding disadvantageous leakage of the solvated AAC through the micelles; and (d) optionally, an anionic surfactant to enhance the close packing of the micelles, thereby rendering the compositions more stable as evidenced by the presence of a clear, homogeneous liquid phase; wherein (a)+(c)+(d) are present in an amount of about 2–90%, preferably 10–80%, by weight of the composition; and (b) is present in an amount of about 1–90%, preferably 5–85%, by weight of the composition.

In the MEC, the weight ratio of AAC to (a)+(c)+(d) is about 1:1 to 1:20, preferably 1:3 to 1:10; and the AAC to (b) is about 1:0.1 to 1:90, preferably 1:0.5 to 1:5.

DETAILED DESCRIPTION OF THE INVENTION

The aqueous microemulsion usually comprises about 0.01–20 parts by weight of the microemulsion concentrate and about 80–99.99 parts by weight of water, the degree of dilution being determined by the desired concentration of the AAC for the end-use application.

AAC's normally take the form of water-immiscible or oily liquids and/or solids. Suitable agriculturally active chemicals which can be used with the present invention include insecticides, such as, cyclocompounds, carbamates, animal and plant derivatives, synthetic pyrethroids, diphenyl compounds, non-phosphates, organic phosphates, thiophosphates, and dithiophosphates. (See *Agricultural Chemicals,* Book I, *Insecticies,* 1989 Revision by W. T. Thomso, Thomson Publications.) Typical of the insecticides are:

| | |
|---|---|
| cyclocompounds: | 6,7,8,9,10,10-hexachloro-1,5,5a,6,9,9a-hexahydro-6,9-methano-2,4,3-benzodioxathiepin-3-oxide benzo-diooxathiepin-3-oxide |
| animal and plant derivatives: | chlorinated hydrocarbons derived from Southern pine; naturally occurring lactone glycoside; |
| synthetic pyrethroids: | (±) alpha-cyano-3-phenoxybenzyl (±) cis, trans 3-(2,2-dichlorovinyl)-2,2-dimethyl cyclopropane carboxylate; (±) cyano (3-phenoxyphenyl methyl (±)-4-(difluoromethyoxy) alpha-(1-methylethyl) benzene acetate; D-allethrin permethrin tetramethrin cypermethrin piperonyl butoxide (synergist) |
| phenoxy compounds and non-phosphate: | 2,2-bis(p-methoxy phenyl)-1,1,1,trichloroethane; 1,3,5,tri-n-propyl-1,3,5-triazine-2,4,6 (1H,3H,5H) trione; ethyl (2E, 4E)-3,7,11-trimethyl- 2,4-dodeca dienoate; 1-decycloxy 4-[(7-oxa-oct-4-ynyl)]-oxybenzene; |
| organic phosphates: | dimethyl phosphate ester of 3-hydroxy-N,N-dimethyl-cis-crotonamide; 2-chloro-1-(2,4-dichloro phenyl) vinyl diethylphosphate; 4-(methyl thio) phenyl dipropyl phosphate; |
| thiophosphates: | 0,0-diethyl-0-4-nitrophenyl phosphorothioate; 0,0-diethyl-0-(2,isopropyl-6-methyl-5-pyrimidinyl) phosphorothioate; 2-diethylamino-6-methyl pyrimidine-4-yl dimethyl phosphorothioate; |
| dithiophosphates: | 0,0-dimethyl phosphorodithioate ester of diethylmrcapto succinate; 0-ethyl-S-phenyl ethyl phosphorodithioate. |

Typical fungicides include (See *Agricultural Chemicals,* Book IV, *Fungicides,* 1989 Revision, W. T. Thomson, Thomson Publications, Fresno, Calif. 93791):

| | |
|---|---|
| organic compounds: | 2,5-dimethyl-N-Cyclohexyl-N-methoxy-3-furan carboxamide; 5-Ethyoxy-3-trichloromethyl-1,2,4-thiadiazole; 3-(2-methyl piperidino) propyl 3,4-dichlorobenzoate; N,N'-(1,4-piperazinediyl bis (2,2,2-trichloro) ethylidene) bis formamide; Tetramethyl thiuram disulfide; 0-Ethyl-S,S,diphenyl-dithiophosphate; 5,10-dihydro-5,10-dioxo naphtho (2,3,9)-p-dithiin-2,3-dicarbonitrile; 2-(Thiocyano methyl thio) benzothiazole; α-2-(4-chlorophenyl) ethyl]-α-(1,1-dimethyl ethyl)-1 H-1,2,4-triazole-1-ethanol; |
| morpholines: | N-tridecyl-2,6-dimethyl morpholine; 4-N-dodecyl-2,6-dimethyl morpholine; |

Typical fumigants, growth regulators, repellents, and rodenticides include (See *Agricultural Chemicals,* Book III, *Fumigants,* 1988–1989 Revision, W. T. Thomson, Thomson Publications, Fresno, Calif. 93791):

| | |
|---|---|
| growth regulants: | 1,2 Dihydro-6-ethyoxy-2,2,4-trimethylquinoline; (2-chloroethyl) phosphoric acid; |

| | |
|---|---|
| | 4-[acetamino) methyl]-2-chloro-N (2,6-diethyl phenyl acetamide; Benzoic acid, 3,6 dichloro-2-methoxy,2-ethoxy-1-methyl-2-oxo ethyl ester; |
| repellants: | 0,0-dimethyl-0-[(4-methyl thio)-m-tolyl]phosphorothioate; Tetriary butyl-sulfenyl dimethyl dithio carbamate; |
| seed softener: | 2-chloro-6-(trichlomethyl) pyridine; 5-ethoxy-3-trichloromethyl-1,2,4-thiadiazole; N-phenyl-N'-1,2,3-thiadiazol-5-yl urea; |

Pesticides may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into two groups. The first group includes those which are oily liquids at ambient temperatures and are immiscible with water. Specific pesticides include:

Common esters of 2,4-dichlorophenoxyacetic acid,
Common esters of 2,4,5-trichlorophenoxyacetic acid,
Common esters of 2-(2,4-dichlorophenoxy) propionic acid,
Common esters of 2-(2,4,5-trichlorophenozy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: 0,0-diethyl-0-2,5-dichloro-4-bromophenyl thionophosphate,
N-(2-mercaptoethyl) benzene-sulfenamide (BETASAN®),
Isobornyl Thiocyanoacetate (Thanite®),
Ioxynil ester of octanoic acid,
Molinate S-ethyl hexahydro-1 H - azepine-1-carbothioate,
PP 511 0,0-dimethyl-(2-diethylamine 4-methyl-6-pyrimidinyl) carbamate,
PP 2II 0,0-diethyl O-(2-diethylamine-4-methyl-6-pyrimidinyl) phosphorocarbamate, Chlordane
5-Ethoxy-3-(trichlorometyl)-1,2,4-thiadiazole (TERRAZALE®),
Ethyl-s-s-dipropyl-phosphodithionate (MOCAP®),
Malathion (S-(1,2-dicarboxyethyl)-0,0-dimethyl phosphorodithioate),
Diazinon (0,0-diethy1,0-(2-isopropyl-4-methyl-6-pyrimidinyl) phosphorothioate,
O-Ethyl-S-phenyl-ethylphosphonodithioate (DYFONATE®),
Toxaphene (Octachlorocamphene),
Bromoxynil (3,5-dibromo-4-hydroxy benzonitrile ester of n-octanoic acid,
2-chloro-N-2,6-diethylphenyl-N-methoxymethylacetamide (LASSO®), The second group comprises those pesticides which are solids at ambient temperatures and for all practical purposes, insoluble in water.

2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dichlorophenyl)-1-methoxy-1 methyl urea
Atrazine (2-chloro-4-ethylamino-6 isopropylamino-s-trriazine) Simazine (2-chloro-4,6,-bis (ethylamino)-s-triazine
Dodine (D-dodecylguanidine acetate)
Thiram (tetramethylthiuram disulfide)
N-(mercaptomethyl)phthalimide s-(o,o dimethylphosphoro-dithioate) (IMIDAN®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl)-dimethyl phosphorothiolthionate)
Barban (4-chloro-2 butynyl m-chlorocarbanilate)
Tricumba 2-methoxy-3,5,6-trichlorobenzoic acid
Trifluralin (2,6-dinitro-N,N-dipropyl-4-trifluoromethylamiline) (2,3 dihydro-5-carboxanilido-6-methyl-1,4-oxathiin) (VITAVAX®)
2,4-dichlorophenoxyacetic acid
4-(4-chloro-2 methylphenoxy) butyric acid
2-(2,4-dichlorophenoxy) propionic acid
Ioxynil: 3,5 diiodo-4-hydroxybenzonitrile
Bromoxynil: 3,5 dibromo-4-hydroxybenzonitrile
Methoxychlor: 2,2,-Bis(p-methoxyphenyl)-1,1-trichloroethane
PP 781: 4(2-chloro phenylhydrazono)-3-methyl-5-isoxazolone*
PP 675: 5-butyl-2-dimethylamino-4-hydroxy-6-methyl pyrimidine*
PP 149: 5-n-butyl-2 ethylamino-4-hydroxy-6 methyl-pyrimidine*

*Manufactured by Imperial Chemical Industries Limited

C 6313 N'-(4-bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N'-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclo-pentapyrimidine-2,4-(3H,5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N'-dimethylurea
Neburon N-butyl-N'-(3,4-dichlorophenyl)-N-methylurea
NIA 11092 1,1-dimethyl-3-[3-(n-t-butyl carbamyloxy)-phenyl]urea
Mecoprop 2-(4-chloro-2 methylphenoxy)propionic acid
Monolinuron N'-(4-chlorophenyl)-N-methoxy-N-methylurea
Nitrofen 2,4-dichlorphenyl 4-nitrophenylether
Propanil N-(3,4-dichlororphenyl)propionamide
Pyriclor 2,3,5-trichloro-4-pyridinol Solan 3'-chloro-2-methyl-p-volerotoluidide Terbacil 5-chloro-3-t-butyl-6-methyluracil
UC 22463 (SIRMATE)-3,4-dichlorobenzyl N-methylcarbamate
WL 9385 2-Azido-4-ethylamino-6-t-butylamino-s-triazine
Propachlor 2-chloro-N-isopropylacetanilide
50144 2-chloro-N-2,6-diethylphenyl-N-methoxymethylacet-amide
CP 31675 2-chloro-N-(2 methyl-6-t-butylphenyl)acetamide
Cypromid 3',4'-dichlorocyclopropane carboxanilide
Fenuron NN-dimethyl-N'phenylurea
Chlorbromuron N'-(4-bromo-3-chlorophenyl)-N-methoxy-N-methylurea
Ametryne 2-methylmercapto-4-ethylamino-6-isopropyl-amino-s-triazine
Prometryne 2-methylmercapto-4,6-bisisopropyl amino-s-triazine
DCPA dimethyl 2,3,5,6, tetrachloroterephthalate
Benefin N-butyl-N-ethyl-2,2,2-trifluoro-2,6-dinitro-p-toluidine
Nitralin 2,6-dinitro-4-methylsulfonyl-NN-dipropyl-aniline
PP 493 2,6-difluoro-3,5-dichloro-4-hydroxy pyridine
CNP 2,4,6-trichlorophenyl-4'-nitrophenyl ether
Pentachloro nitrobenzine
1-(butile carbamoyl)-2-benzimidazol carbamic acid, methyl ester (BENLATE®)]

Representative $C_6-C_{18}$ alkyl pyrrolidones include N-octylpyrrolidone and N-isooctylpyrrolidone.

Representative $C_1-C_4$ alkyl pyrrolidones include N-methylpyrrolidone, N-ethylpyrrolidone and N-butylpyrrolidone.

Representative nonionic surfactants include:
Alkylphenol ethoxylated alcohol having an HLB $\geq 6$, e.g., nonylphenol ethoxylated alcohol with 9 EOs - (Igepal® CO-630); and
Ethylene oxide (EO)/propylene oxide (PO)/EO block copolymers, e.g., (2 EO/16 P012 EO-$H_2O$ - (Pegal® L-31).

Representative anionic surfactant include nonylphenol ethoxylated phosphate esters with 9 EOs -(Gafac® RE-610).

In this invention, the suitable amount of the $C_6-C_{18}$ alkyl pyrrolidone (higher lactam) can form micelles of the water-insoluble, agriculturally active chemicals in water which are solvated by the presence of the higher lactam in the micelles. The $C_1-C_4$ alkyl pyrrolidone (lower lactam) is present in the micelles complexed with the higher lactam in an amount which is sufficient to solubilize the active chemical in the micelles. The nonionic surfactant having an HLB of $\geq 6$ is present in an amount sufficient to also complex with the higher lactam and thereby to reduce the size of the micelle to about 0.005 to 0.5 microns, thus precluding any disadvantageous leakage of the solvated chemical through the micelles. Optionally, an anionic surfactant may be present in the system to enhance the close packing of the micelles thereby rendering the compositions even more stable as evidenced by the presence of a clear, homogeneous liquid phase.

In accordance with the invention, a Two-Part Microemulsion System (TPMS) is provided which comprises, as one part, the IMC and, as a second part, the AAC. While the $C_1-C_4$ alkyl pyrrolidone is preferably included in the IMC, it may be used as a solvent for the AAC and be present in the second part of the TPMS.

The Microemulsion Concentrate (MEC) is obtained by mixing both parts of the TPMS to provide a suitable concentration of about 2-30 parts of the AAC and about 70-98 parts of the TPMS.

The MEC may be stored, or diluted with water and stored until use, or diluted with water just before use. Upon dilution of the MEC with water, a Water Based Microemulsion (WBME), or simply, an Aqueous Microemulsion (AME), is formed, which contains from a few ppm to about 2% by weight of the AAC. Generally, water is present in the AME in an amount of about 80-99.99% by weight.

The end-use aqueous microemulsion system of the AAC herein is uniquely thermodynamically stable, and has low toxicity; the matrix is biodegradable, and has wide applicability with minor modifications of the ratio of its components. The WBME/AME system has very low turbidity $\leq 20$ NTU at 10-25° C.) but becomes clear when cooled to ambient temperature.

EXPERIMENTAL PROCEDURES AND RESULTS

The aqueous microemulsions (AME) of the invention were prepared by alternate procedures (a) and (b) which are described below:

Procedure a

The IMC was prepared by mixing predetermined amount of the $C_6-C_{18}$ alkyl pyrrolidone, the defined nonionic surfactants, optionally with an anionic surfactant, and preferably with the $C_1-C_4$ alkyl pyrrolidone. Then the AAC was added and the mixture was shaken until the AAC dissolved or the mixture became homogeneous, typically in about 30 minutes to 2 hours, which resulted in formation of an MEC. Then the MEC was diluted with a predetermined amount of water to form the AME. Water for dilution was either deionized water or WHO standard hard water (342 ppm as $CaCO_3$ equivalent).

Procedure (b)

The IMC was added to an AAC dissolved in a $C_1-C_4$ alkyl pyrrolidone to form the MEC, and water was added to form the WBME.

The aqueous microemulsion compositions of the invention made according to procedures (a) and (b) are summarized in TABLES 1 and 2 below, wherein the component amounts are in grams. The stability properties of such compositions at room temperature after standing at room temperature for a considerable period also is included therein.

TABLE 1

| EXAMPLES | 1 | 2 | 3 | 4 | 5 | 6 | 7 |
|---|---|---|---|---|---|---|---|
| Inert matrix Composition | | | | | | | |
| N-Octylpyrrolidone | 0.63 | 0.63 | 1.66 | 0.63 | 0.63 | 0.5 | 0.4 |
| N-Isooctylpyrrolidone | | | | | | | |
| Pegol-L31 | 0.63 | 0.63 | | 0.63 | 0.63 | | |
| Igepal CO-630 | 3.75 | 3.75 | 1.66 | 3.75 | 3.75 | 1 | 1.2 |
| Gafac RE-610 | | | 1.66 | | | 0.5 | 0.4 |
| N-Methylpyrrolidone | 5 | 1.8 | 10 | 10 | 5 | 1.35 | 1.35 |

TABLE 1-continued

| EXAMPLES | 1 | 2 | 3 | 4 | 5 | 6 | 7 |
|---|---|---|---|---|---|---|---|
| N-Ethylpyrrolidone | | | | | | | |
| N-Butylpyrrolidone | | | | | | | |
| Microemulsion Concentrate | | | | | | | |
| D-Allethrin | 0.05 | | | | | | |
| Permethrin | 0.15 | | | | | 0.15 | 0.15 |
| Tetramethrin | 0.2 | 0.2 | | | | | |
| Piperonyl Butoxide | 1 | | 1 | 1 | 1 | | |
| Cypermethrin | | | | | | | |
| Water-Based Microemulsion | | | | | | | |
| Water d/h | 89.6 | 93.2 | 84.02 | 83.99 | 88.99 | 96.5 | 96.5 |
| | 100 | 100 | 100 | 100 | 100 | 100 | 100 |
| Properties of Aqueous Microemulsion at Room Temperature | | | | | | | |
| at 0 hr. | clear | clear | clear | clear | clear | clear | clear |
| 24 hr. | clear | clear | clear | clear | clear | clear | clear |
| 2 days. | clear | clear | clear | clear | clear | clear | clear |
| 1 week | clear | clear | clear | clear | clear | clear | clear |
| 4 week | clear | clear | clear | clear | clear | clear | clear |
| 2 months | clear | clear | clear | clear | clear | clear | clear | d' means deionized water, 'h' means standard hard water, 342 ppm hardness

TABLE 2

| EXAMPLES | 8 | 9 | 10 | 11 | 12 | 13 | 14 | 15 |
|---|---|---|---|---|---|---|---|---|
| Inert matrix Composition | | | | | | | | |
| N-Octylpyrrolidone | | 0.4 | 0.4 | 0.1 | 0.13 | 0.2 | 0.09 | 0.094 |
| N-Isooctylpyrrolidone | 0.6 | | | | | | | |
| Pegol-L31 | 1.8 | 1.2 | 1.2 | 0.1 | 0.13 | 0.2 | 0.09 | 0.094 |
| Igepal CO-630 | | | | | | 1.2 | 0.53 | 0.57 |
| Gafac RE-610 | 0.6 | 0.4 | 0.4 | 0.1 | 0.13 | | | |
| N-Methylpyrrolidone | 1.35 | | | 0.45 | 0.45 | 0.45 | 0.2 | 0.142 |
| N-Ethylpyrrolidone | | 1.35 | | | | | | |
| N-Butylpyrrolidone | | | 1.35 | | | | | |
| Microemulsion Concentrate | | | | | | | | |
| D-Allethrin | | | | 0.05 | 0.05 | 0.05 | | |
| Permethrin | 0.15 | 0.15 | 0.15 | | | | | |
| Tetramethrin | | | | | | | | |
| Piperonyl Butoxide | | | | | | | | |
| Cypermethrin | | | | | | | 0.1 | 0.1 |
| Water-Based Microemulsion | | | | | | | | |
| Water d/h | 95.5 | 96.5 | 96.5 | 99.2 | 99.1 | 97.9 | 98.9 | 99 |
| | 100 | 100 | 100 | 100 | 100 | 100 | 100 | 100 |
| Properties of Aqueous Microemulsion at Room Temperature | | | | | | | | |
| at 0 hr. | clear | clear | clear | clear | clear | clear | clear | |
| 24 hr. | clear | clear | clear | clear | clear | clear | clear | |
| 2 days. | clear | clear | clear | clear | clear | clear | clear | |
| 1 week | clear | clear | clear | clear | clear | clear | clear | |
| 4 week | clear | clear | clear | clear | clear | clear | clear | |
| 2 months | clear | clear | clear | clear | clear | clear | clear | | d' means deionized water, 'h' means standard hard water, 342 ppm hardness

What is claimed is:

1. An inert matrix composition suitable for forming a clear, efficacious, microemulsion concentrate including about 2-30% of a water-insoluble, agriculturally active chemical and, upon dilution of said concentrate with water, an aqueous microemulsion, both of which are stable for an extended period of time, consisting essentially of:
   (a) a $C_6$-$C_{18}$ alkyl pyrrolidone in an amount of about 2-90% by weight of the composition less (c) and (d) if present, sufficient to form solvated micelles of the agriculturally active chemical;
   (b) a $C_1$-$C_4$ alkyl pyrrolidone in an amount of about 1-90% by weight of the composition sufficient to complex with said $C_6$-$C_{18}$ alkyl pyrrolidone and to solubilize said chemical in said micelles;
   (c) a nonionic surfactant having an HLB of $\geq 6$ in an amount of about 2-90% by weight of the composition less (a) and (d) if present, sufficient to also complex with said $C_6$-$C_{18}$ pyrrolidone to reduce said micelle size to about 0.005-0.5 microns thereby precluding disadvantageous leakage of said solvated chemical through said micelles; and
   (d) optionally, an anionic surfactant in an amount of 2-90% by weight of the composition less (a) and (c) to enhance the close-packing of the micelles thereby rendering the compositions more stable as evidenced by the presence of a clear, homogeneous liquid phase.

2. An inert matrix composition according to claim 1 wherein (a) is an N-octyl pyrrolidone; (b) is N-methyl pyrrolidone; (c) has an HLB of 6-20; and (d), if present, is a nonylphenyl ethoxylated phosphate ester.

3. An inert matrix composition according to claim 1 wherein (c) includes a plurality of nonionic surfactants of differing HLB values.

4. An inert matrix composition according to claim 1 wherein (d) is present therein.

5. An inert matrix composition according to claim 1 for an agriculturally active chemical in an amount of about 5–25% by weight; said micelles are about 0.01–0.1 microns in size; the (a)+(c)+(d) components are present in an amount of about 10–80%, and (b) is present in an amount of about 5–85%.

6. An inert matrix composition according to claim 1 where (c) includes a hydrophobic portion within said micelle phase and a hydrophilic portion in said water phase.

7. A two-part microemulsion system which comprises, as one part, the inert matrix composition of claim 1 and, as the second part, an agriculturally active chemical, wherein component (b) of said inert matrix composition can be present in either or both of said parts.

8. A microemulsion concentrate suitable for forming a clear, efficacious aqueous microemulsion of an agriculturally active chemical upon dilution with water, which is stable for an extended period of time, at or below room temperature, consisting essentially of a mixture of:
   (i) the two-part microemulsion system of claim 7, and
   (ii) about 2–30% by weight of said agriculturally active chemical;
   wherein the weight ratio of (ii) to (a)+(c)+(d) to about 1:1 to 1:20, and (ii) to (b) is about 1:0.1 to 1:90.

9. A microemulsion concentrate according to claim 8 wherein (ii) is about 3–20%; the weight ratio of (ii) to (a)+(c)+(d) is about 1:3 to 1:10; and (ii) to (b) is about 1:0.5 to 1:5.

10. A clear, efficacious, aqueous microemulsion of a water-insoluble, agriculturally active chemical which is stable at or below room temperature for an extended period of time consisting essentially of:
   about 0.01–20 parts by weight of the microemulsion concentrate of claim 8, and about 80–99.99 parts of water.

* * * * *